US012135363B2

(12) United States Patent
Rehwald et al.

(10) Patent No.: US 12,135,363 B2
(45) Date of Patent: Nov. 5, 2024

(54) SHOT-WISE INVERSION TIME ADAPTATION FOR MULTI-SHOT INVERSION RECOVERY IMAGING

(71) Applicants: Siemens Healthineers AG, Erlangen (DE); Duke University, Durham, NC (US)

(72) Inventors: Wolfgang G. Rehwald, Chapel Hill, NC (US); Raymond J. Kim, Chapel Hill, NC (US); Enn-Ling Chen, Chapel Hill, NC (US)

(73) Assignees: Siemens Healthineers AG, Forchheim (DE); Duke University, Durham, NC (US)

( * ) Notice: Subject to any disclaimer, the term of this patent is extended or adjusted under 35 U.S.C. 154(b) by 106 days.

(21) Appl. No.: 18/049,292

(22) Filed: Oct. 25, 2022

(65) Prior Publication Data

US 2023/0132314 A1    Apr. 27, 2023

Related U.S. Application Data

(60) Provisional application No. 63/271,832, filed on Oct. 26, 2021.

(51) Int. Cl.
*G01V 3/00* (2006.01)
*G01R 33/483* (2006.01)
(Continued)

(52) U.S. Cl.
CPC ..... *G01R 33/5608* (2013.01); *G01R 33/4835* (2013.01); *G01R 33/5611* (2013.01); *A61B 5/055* (2013.01)

(58) Field of Classification Search
CPC .............. G01R 33/3415; G01R 33/543; G01R 33/5659; G01R 33/36; A61B 5/055
(Continued)

(56) References Cited

U.S. PATENT DOCUMENTS 10,591,568 B2    3/2020  Rehwald et al.
2005/0245809 A1*  11/2005  Wolff ................... G01R 33/561
                                                     600/410
(Continued)

FOREIGN PATENT DOCUMENTS

DE    102005027963 B3 * 12/2006  ............. A61B 6/032
JP      2008068089 A  *  3/2008  ........ G01R 33/4818

OTHER PUBLICATIONS

Kim, Raymond J., et al. "Relationship of MRI delayed contrast enhancement to irreversible injury, infarct age, and contractile function." Circulation 100.19 (1999): 1992-2002.
(Continued)

*Primary Examiner* — Walter L Lindsay, Jr.
*Assistant Examiner* — Frederick Wenderoth

(57) ABSTRACT

A system and method comprises execution of a segmented magnetic resonance imaging pulse sequence, the pulse sequence including a plurality of shots, each of the plurality of shots including an inversion recovery preparation pulse and acquiring a respective segment of k-space lines, wherein each shot comprises a different inversion time between a peak of the inversion recovery pulse and a midpoint of the acquisition of the respective segment of k-space lines, and reconstruction of an image based on the acquired respective segments of k-space lines. In some aspects, the k-space lines acquired by each shot are consecutive in a phase encoding direction of k-space and each shot acquires the segments of k-space lines acquired by prior shots in the sequence, and a time delay between the inversion recovery preparation pulse and acquisition of a first segment for each shot is equal. In other aspects, each shot acquires its respective segment using interleaved reordering and the time delay between the inversion recovery preparation pulse and acquisition of the respective segment for each shot is different.

20 Claims, 13 Drawing Sheets

(51) Int. Cl.
G01R 33/56 (2006.01)
G01R 33/561 (2006.01)
A61B 5/055 (2006.01)

(58) Field of Classification Search
USPC .......................................................... 324/309
See application file for complete search history.

(56) References Cited

U.S. PATENT DOCUMENTS

| | | | | |
|---|---|---|---|---|
| 2010/0219829 | A1* | 9/2010 | Rehwald | G01R 33/4818 324/309 |
| 2011/0074417 | A1* | 3/2011 | Kitane | A61B 5/0263 324/309 |
| 2016/0132746 | A1* | 5/2016 | Saranathan | A61B 5/742 382/131 |
| 2017/0364252 | A1* | 12/2017 | Deshpande | A61B 5/055 |

OTHER PUBLICATIONS

Simonetti, Orlando P., et al. "An improved MR imaging technique for the visualization of myocardial infarction." Radiology 218.1 (2001): 215-223.

Kellman, Peter, et al. "Motion-corrected free-breathing delayed enhancement imaging of myocardial infarction." Magnetic Resonance in Medicine: An Official Journal of the International Society for Magnetic Resonance in Medicine 53.1 (2005): 194-200.

Serai, Suraj D., et al. "Newly developed methods for reducing motion artifacts in pediatric abdominal MRI: tips and pearls." American Journal of Roentgenology 214.5 (2020): 1042-1053.

Zaitsev, Maxim, Julian Maclaren, and Michael Herbst. "Motion artifacts in MRI: A complex problem with many partial solutions." Journal of Magnetic Resonance Imaging 42.4 (2015): 887-901.

Wildgruber, M., et al. "Inversion-recovery single-shot cardiac MRI for the assessment of myocardial infarction at 1.5 T with a dedicated cardiac coil." The British journal of radiology 85.1017 (2012): e709-e715.

Xue, Hui, et al. "Motion correction for myocardial T1 mapping using image registration with synthetic image estimation." Magnetic resonance in medicine 67.6 (2012): 1644-1655.

Kellman, Peter, et al. "Phase-sensitive inversion recovery for detecting myocardial infarction using gadolinium-delayed hyperenhancement." Magnetic Resonance in Medicine: An Official Journal of the International Society for Magnetic Resonance in Medicine 47.2 (2002): 372-383.

Sievers, Burkhard, et al. "Rapid detection of myocardial infarction by subsecond, free-breathing delayed contrast-enhancement cardiovascular magnetic resonance." Circulation 115.2 (2007): 236-244.

Huber, Armin, et al. "Single-shot inversion recovery TrueFISP for assessment of myocardial infarction." American Journal of Roentgenology 186.3 (2006): 627-633.

* cited by examiner

SHOT-WISE INVERSION TIME ADAPTATION FOR MULTI-SHOT INVERSION RECOVERY IMAGING

CROSS-REFERENCE TO RELATED APPLICATIONS

This application claims priority to U.S. Provisional Patent Application No. 63/271,832, filed Oct. 26, 2021, the disclosure of which is incorporated herein by reference for all purposes.

BACKGROUND

A Magnetic Resonance (MR) scanner generates images of patient anatomy using timed sequences of RF pulses. MR imaging is useful in scenarios requiring high contrast between different soft tissues. Cardiac MR (CMR) imaging is increasingly used to non-invasively evaluate myocardial structure and function without requiring ionizing radiation as in other imaging modalities.

CMR imaging often uses a segmented inversion recovery (IR)-prepared sequence which follows the injection of a T1-shortening Gadolinium-based contrast agent. Such a sequence, known as a "delayed enhancement" (DE) or "late Gadolinium enhancement" (LGE) sequence, produces T1-weighted images in which viable (i.e., healthy, living) myocardium appears dark and infarcted (i.e., dead) myocardium appears bright. The sequence also exhibits high spatial resolution and excellent sensitivity to infarcted myocardium.

Generation of a high-resolution LGE image requires more data than can be acquired in a single data readout (i.e., shot), especially for images of moving structures such as the heart. For example, an image produced from the data of a single shot would exhibit poor temporal resolution, and intricate cardiac features would appear blurred. Therefore, each image is reconstructed from raw data acquired during multiple shots wherein each shot is taken with precise temporal resolution (i.e., in the same cardiac phase but in a different heartbeat). Each of the multiple shots acquires a different subset of all the lines of the raw data space known as "k-space".

More specifically, the data acquired by a single shot is not image data but is frequency-encoded data in k-space. k-space is defined by two orthogonal directions, the phase encoding (PE) direction and the frequency encoding (FE) direction. Different regions of k-space contain different image properties. For example, the center of k-space contains image brightness and contrast information, and the edges of k-space contain sharpness and detail information. A two-dimensional Fourier Transform (FT) may be used to calculate an image from acquired k-space data.

FIG. 1 illustrates a portion of an IR-prepared segmented sequence as is known in the art. IR pulse 100 is applied and then readout pulses 150 are applied to successively acquire multiple PE lines in a single shot. It may be assumed that the FE data points of each PE line are acquired instantaneously. The T1 recovery due to the IR preparation modulates the signal of the acquired PE lines, as shown by magnetization signal $M_z$. This results in a different modulation corresponding to each PE line (i.e., echo) which is acquired by the single shot.

The relationship between the temporal order in which PE lines are acquired and their specific location in k-space is known as "reordering". In the context of IR-prepared imaging, reordering affects the image contrast, specifically T1 contrast, and the robustness of the acquisition to motion and flow. Conventional types of reordering include continuous reordering and interleaved reordering.

According to contiguous reordering, each shot acquires a set or segment of m contiguous PE lines, such that two segments from consecutive shots share one border in k-space. FIG. 2A illustrates contiguous reordering as is known in the art. Segment 1 is acquired in a first shot, including PE lines 1 through m. A second shot acquires segment 2, which includes PE lines m+1 to 2m. For a k-space consisting of n*m lines, n segments are acquired in this manner.

Using contiguous reordering, the different modulation corresponding to each PE line within a segment creates a periodic pattern of the modulation function in the PE direction as shown in FIG. 2B. The pattern creates artificial frequencies in k-space and consequent ghosting in an image which is reconstructed from the acquired k-space lines. The different modulations also create significant signal discontinuities between adjacent segments as shown in FIG. 2B, resulting in additional image artifacts.

As illustrated in FIG. 3A, interleaved reordering refers to the acquisition of a segment of m lines during each shot which do not correspond to a single contiguous region in the PE direction but are instead spaced apart from one another. Assuming a k-space consisting of n*m lines, the m lines of an interleaved-reordered segment in are spaced at a distance of n lines from one another. Accordingly, the entire k-space is traversed in the PE direction by each shot but only m lines out of the total m*n lines are acquired by each shot. After n shots, all m*n lines have been acquired.

As illustrated in FIG. 3B, interleaved reordering does not introduce a periodic modulation pattern and reduces the discontinuities between adjacent segments in k-space in comparison to contiguous reordering. An image generated using interleaved reordering may exhibit fewer artifacts and may appear sharper than a corresponding image generated using contiguous reordering. Therefore, for static objects, interleaved reordering is ubiquitously used in segmented IR-prepared imaging.

However, interleaved reordering is extremely sensitive to motion and flow of the objects to be imaged. Ghosting artifacts may result from even the slightest positional shift between shots, for example due to an imperfect breath hold. Ghosting may also occur in the presence of arrythmia or poor ECG-triggering, which may cause one or more shots of the sequence to be acquired during a different cardiac phase than the other shots. By way of explanation, positional shift modulates the amplitude and phase of the raw data and, if the positional shift is different for each shot and the data acquired by each shot is combined by interleaving, artificial frequencies are introduced into k-space. These artificial frequencies are reflected as replication of structures in image space, i.e., ghosting.

Correction of such interleaved-reordered data in k-space or image space has not been successfully performed and may be impossible, partially because the motion causing the positional shifts is non-rigid. Whereas non-rigid motion correction exists for single shot images, non-rigid motion correction is incompatible with images reconstructed from interleaved data. Each set of interleaved k-space data reconstructs into an aliased image wherein different sections of the imaged field of view in the PE direction are superimposed on one another, known as aliasing. Since each region has experienced a different non-rigid positional shift, no single motion correction of an aliased image can correct all sections. Moreover, due to the sensitivity of interleaved PE lines to amplitude and phase changes, motion-corrected interleaved data typically produces ghosting in image space.

Conversely, contiguous reordering is quite motion-robust. However, as described above, the combination of IR-preparation with contiguous reordering causes artifacts unrelated to motion. Although interleaved reordering may be employed to reduce these artifacts, this approach results in motion-sensitivity, as also described above.

Systems to efficiently generate high-quality, motion-robust images using an IR-prepared segmented pulse sequence are desired.

DETAILED DESCRIPTION

The following description is provided to enable any person in the art to make and use the described embodiments. Various modifications will remain apparent to those in the art.

Embodiments provide a reordering and inversion time (TI) scheme that addresses the motion- and flow-sensitivity of conventional techniques, while being compatible with IR-preparation sequences.

It is traditionally counterintuitive to use contiguous reordering for a segmented IR-prepared sequence due to the above-described incompatibility of contiguous reordering with IR-preparation. Some embodiments overcome this incompatibility by using a different TI for each shot and by acquiring, in each shot, a different number of "dummy" segments before acquisition of a shot-specific segment to be used in image reconstruction (i.e., a k-space segment). The TI of each shot refers to the time between the peak of an IR preparation pulse and a time at a midpoint of the acquisition of the k-space segment of the shot. Use of a different TI for each shot is also counterintuitive to the common belief that the same TI should be used for all shots of a segmented sequence.

Figure 1:
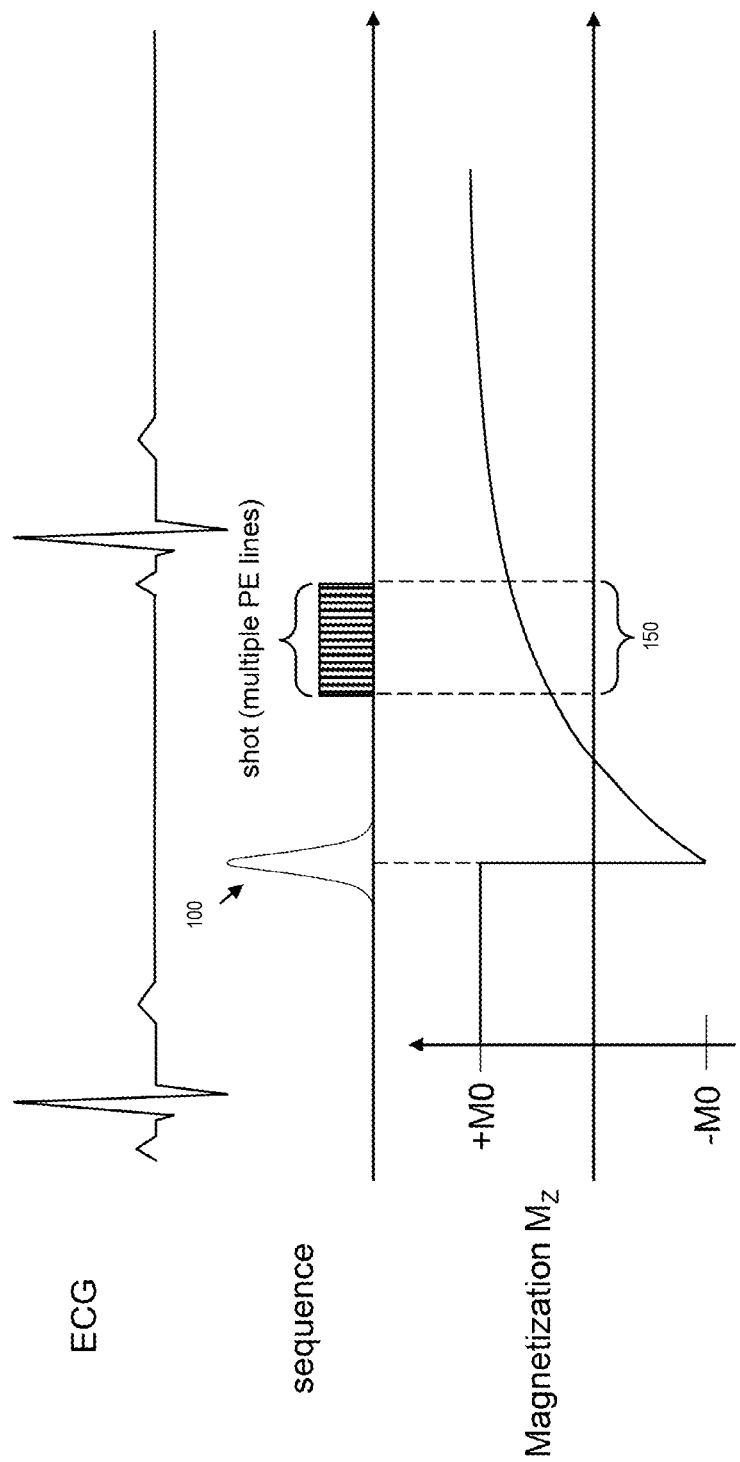
FIG. 1 illustrates a portion of an IR-prepared, segmented pulse sequence.
Figure 2A:
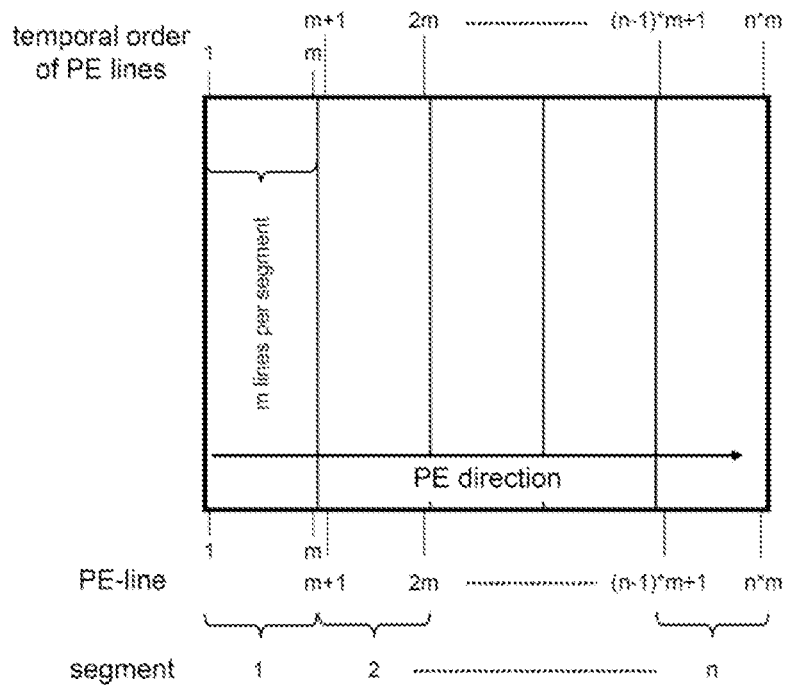
FIG. 2A illustrates contiguous reordering.
Figure 2B:
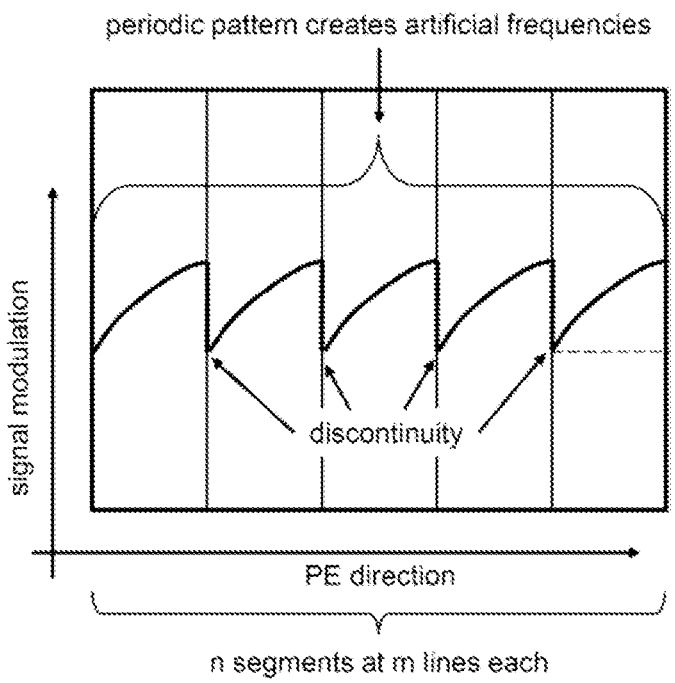
FIG. 2B illustrates modulation discontinuities in k-space segments due to contiguous reordering.

These modifications to a standard contiguous reordering scheme prevent both the periodic modulation pattern and the discontinuities in k-space resulting from standard IR-prepared contiguous reordering and shown in FIG. 2B. Stated differently, the foregoing aspects drive the magnetization at the beginning of the acquisition of each k-space segment to the same amplitude and phase as existed at the end of the k-space segment acquired by the immediately-previous shot. Thus, the signal discontinuity at segment borders is minimized, as is periodic modulation across k-space in the PE-direction.

Embodiments described herein, in essence, reproduce the magnetization behavior of a single shot acquisition (i.e., an acquisition in which all k-space lines desired for imaging are acquired in a single segment across k-space). However, a true single shot acquisition with the same high spatial resolution as the embodiments described herein would exhibit very poor temporal resolution, taking so much time as to include the cardiac motion of a significant portion of a cardiac cycle, for example. The heart would therefore be blurry or unrecognizable in the resulting image. It would not be practical to motion-correct such a poor-quality single shot image because the large number of time points represented in the image would not be separable in post-processing.

Figure 4:
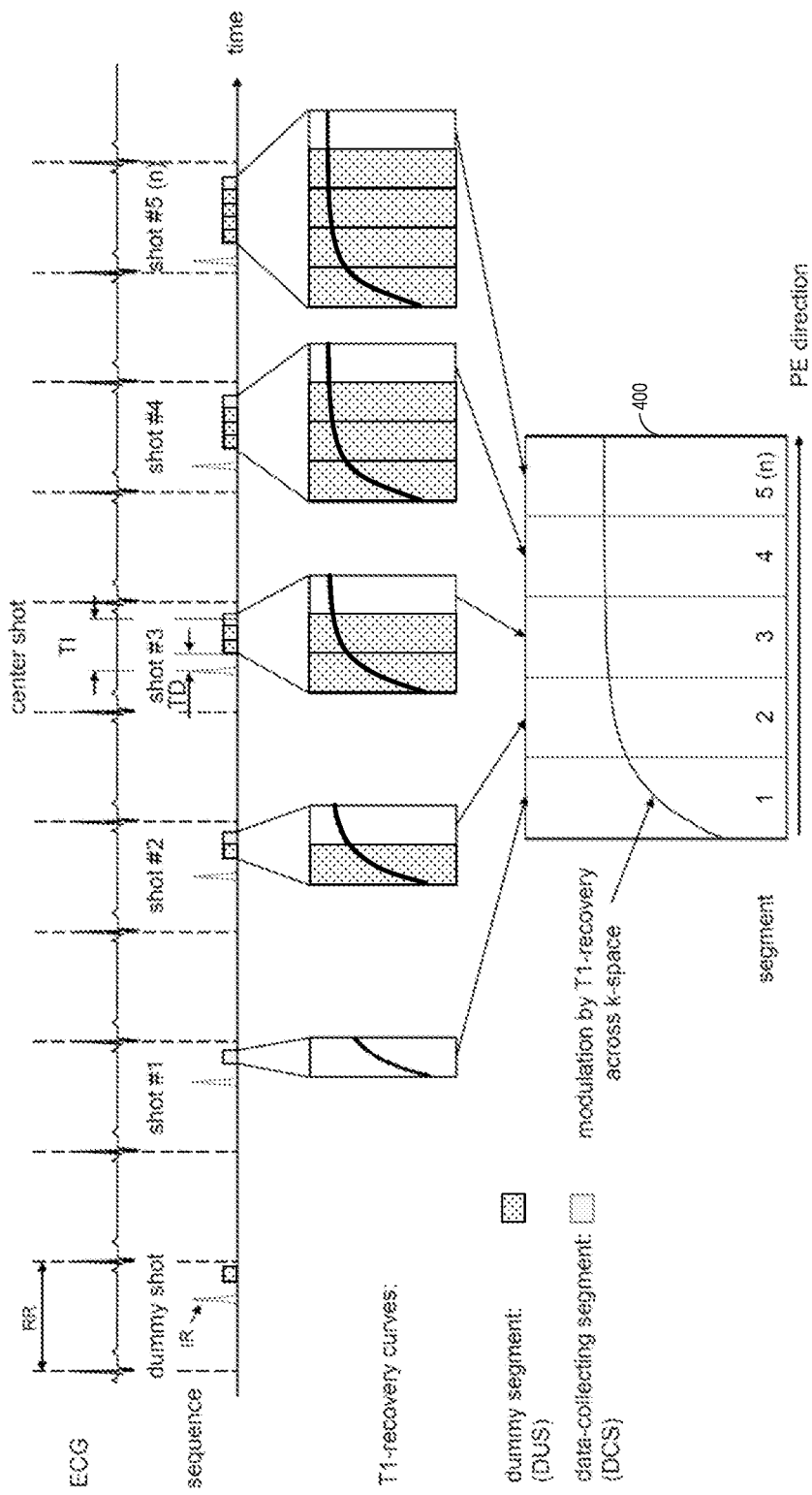
FIG. 4 illustrates an IR-prepared segmented pulse sequence including shot-specific TI values and acquisition of dummy segments according to some embodiments.

FIG. 4 illustrates a pulse sequence according to some embodiments. Each shot acquires k-space lines of one or more segments. The first segment acquired by each shot may be a dummy segment (DUS) or a k-space segment (DCS). The lines of a DUS are acquired in a same manner (e.g., using the same radiofrequency pulses, flip angle, gradient pulses, and timing) as the lines of a DCS, but the lines of a DUS are ignored and not used in subsequent image reconstruction. Each shot acquires one DCS and zero or more DUSs, and the duration of the DCS equals the temporal resolution of the resulting image.

Acquisition of a DCS or DUS according to some embodiments may utilize any suitable type of readout pulses, including but not limited to gradient echo, non-interleaved epi, steady-state free precession, and turbo spin-echo.

According to the FIG. 4 sequence, each shot is separated by a recovery heartbeat (i.e., an R-R interval during which no magnetization pulses are applied). The recovery heartbeat allows magnetization recovery between consecutive shots.

For each shot (#1-#5) in the pulse sequence, the time TD from the peak of the IR pulse to acquisition of the first segment (image or dummy) is fixed. Shot #1 acquires no DUS before its DCS, shot #2 acquires 1 DUS before its DCS, and shot #5 acquires 4 DUS before its DCS. Considering the generic case of n shots resulting in n k-space segments, shot #n acquires (n−1) DUS before its DCS. The time between the IR pulse of a shot to acquisition of the DCS of the shot is therefore different for each shot. Accordingly, the time delay between the ECG's R-wave and the IR pulse is different for each shot, unlike in known sequences using interleaved or continuous reordering.

The IR pulse in some embodiments may comprise a spatially non-selective IR pulse, a spatially selective IR pulse, a wideband IR pulse, a double-IR dark-blood preparation pulse, or any other suitable IR pulse. In some embodiments, a magnetization transfer preparation or a T2-preparation is applied before or after an IR pulse.

The T1-recovery curves of FIG. 4 show that, in each shot, acquisition of one or more DUSs mimics the magnetization recovery as it existed at the end of acquisition of the k-space segment of the previous shot. This mimicry ensures a smooth transition between neighboring segments in k-space, as shown in diagram 400. The particular modulation by T1-recovery across k-space shown in diagram 400 is associated with one specific T1 and varies by T1. Nevertheless, embodiments ensure a smooth transition between segments and prevent periodic patterns for any given T1 species.

In the first R-R interval of FIG. 4, a dummy shot is played with the same timing as used for shot #1, although the dummy shot acquires a DUS rather than a DCS as in shot #1. This dummy shot is generally used in segmented sequences for driving the magnetization to steady state before starting data acquisition. Embodiments are not required to play a leading dummy shot since this shot does not affect the periodicity or the creation of discontinuities of the modulation.

In IR-prepared imaging, TI is defined as the time from the IR pulse to the acquisition of the center line of k-space. A TI may be selected so as to achieve a desired T1-contrast, since the center of k-space contains image brightness and contrast information. In the example of FIG. 4, this TI is used only for shot #3, which acquires segment 3 including the center line of k-space.

According to some embodiments, the shot which acquires the center line of k-space determines the time delay TD between the IR pulse and the first segment of each shot. For example, a TI is selected based on a desired T1-contrast. With reference to shot #3 of FIG. 4, the timing of the acquisition of the center line of k-space (i.e., the center of the DCS) is set at a time point of the R-R interval representing diastole, and the IR pulse for this shot is placed such that the time between the peak of the IR pulse and the center of the DCS is equal to the selected TI. The number of DUSs to be acquired by the shot including this DCS is determined (i.e., two in the case of shot #3) and acquisition of this number of DUSs is scheduled between the IR pulse and the DCS. The time between IR pulse and acquisition of the first DUS of this shot is then determined to be the TD for all shots.

The timing of all other shots is derived therefrom by keeping the acquisition of the DCS of each shot at the same point of the R-R interval (at diastole), inserting acquisition of the required number of preceding dummy segments, and placing the IR pulse at a time TD prior to acquisition of the first segment of the shot. Shot #n is the longest in duration and determines the minimum needed acquisition window. All shots may ideally fit into one R-R interval, but imaging over two or more R-R intervals is possible, which would result in a longer shot and thus higher spatial resolution.

Figure 5:
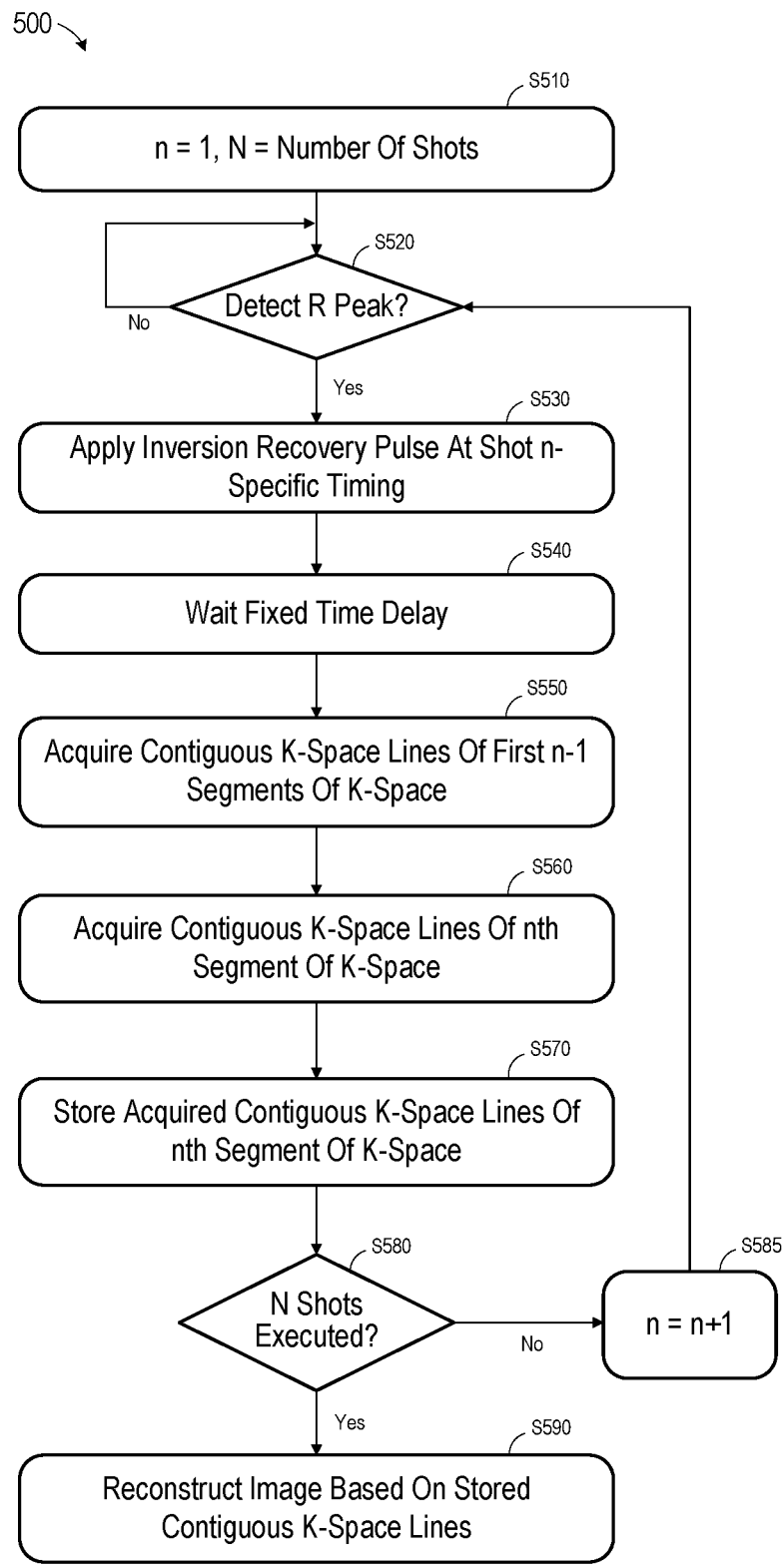
FIG. 5 is a flow diagram of a process to execute the FIG. 4 pulse sequence according to some embodiments.

FIG. 5 comprises a flow diagram of process 500 to execute the FIG. 4 sequence according to some embodiments. In some embodiments, various hardware elements of an MRI scanner execute program code to perform process 500. The steps of process 500 need not be performed by a single device or system.

Process 500 and all other processes mentioned herein may be embodied in executable program code read from one or more of non-transitory computer-readable media, such as a disk-based or solid-state hard drive, a DVD-ROM, a Flash drive, and a magnetic tape, and then stored in a compressed, uncompiled and/or encrypted format. In some embodiments, hard-wired circuitry may be used in place of, or in combination with, program code for implementation of processes according to some embodiments. Embodiments are therefore not limited to any specific combination of hardware and software.

At S510, the shot number n is initialized to 1, where the total number of shots to execute is N. Flow pauses at S520 until an R peak (i.e., the start of a heartbeat interval) is detected. At S530, an IR pulse is applied as is known in the art at a timing specific to the first (n=1) shot. The timing is determined based on the predetermined timing of the DCS of the shot (i.e., at diastole), on the number of DUSs preceding the DCS and their overall acquisition duration, and on the time TD calculated as described above. Accordingly, each IR pulse of the FIG. 4 pulse sequence is applied at a different time interval from its preceding R peak.

Next, process 500 waits at S540 for time TD. Once time TD expires, contiguous k-space lines of the first n−1 segments of k-space are acquired. These n−1 segments are referred to as dummy segments above. Since n currently equals 1 in the present example, no dummy segments are acquired at S550, as shown in FIG. 4.

Contiguous k-space lines of the nth segment of k-space are acquired at S570. Continuing the present example, contiguous k-space lines of segment 1 of k-space are acquired during shot #1, as also shown in FIG. 4.

The contiguous k-space lines acquired at S560 are stored at S570 and it is then determined at S580 whether N shots have been executed. If not, n is incremented at S585 and flow returns to S520 to wait for a next R peak. According to some embodiments, flow pauses at S520 until two R peaks are detected in order to allow a magnetization recovery heartbeat interval to elapse between consecutive shots as illustrated in FIG. 4.

Once a suitable R peak is detected, an inversion recovery pulse is applied at a timing specific to shot #2. This timing must account for acquisition of the one DUS of shot #2 and therefore the inversion pulse is applied earlier in the R-R interval than in shot #1. Flow pauses at S540 for the same time TD as used in shot #1.

One (n−1=1) DUS is acquired at S550, followed by acquisition at S560 of contiguous k-space lines of the second segment of k-space. The contiguous k-space lines of the second segment of k-space are stored at S570.

Flow continues in this manner until five shots have been executed, each with the same TD and different TIs. Each shot acquires and stores contiguous k-space lines of a respective segment of k-space. Accordingly, at S590, an image is reconstructed based on the stored contiguous k-space lines as is known in the art.

Returning to FIG. 3B, the reason for slight ghosting in an interleaved-reordered image are the small yet non-negligible steps in the modulation function at each segment border. Each segment consists of lines acquired in different shots but at the same time point within each shot, also known as the echo position. For example, segment 1 contains data from echo position 1, segment 2 from echo position 2, etc. The time difference between consecutive echo positions is the time to collect one line, known as the echo spacing (ES). This small difference of one ES results in the steps at the segment borders of FIG. 3B.

Figure 6:
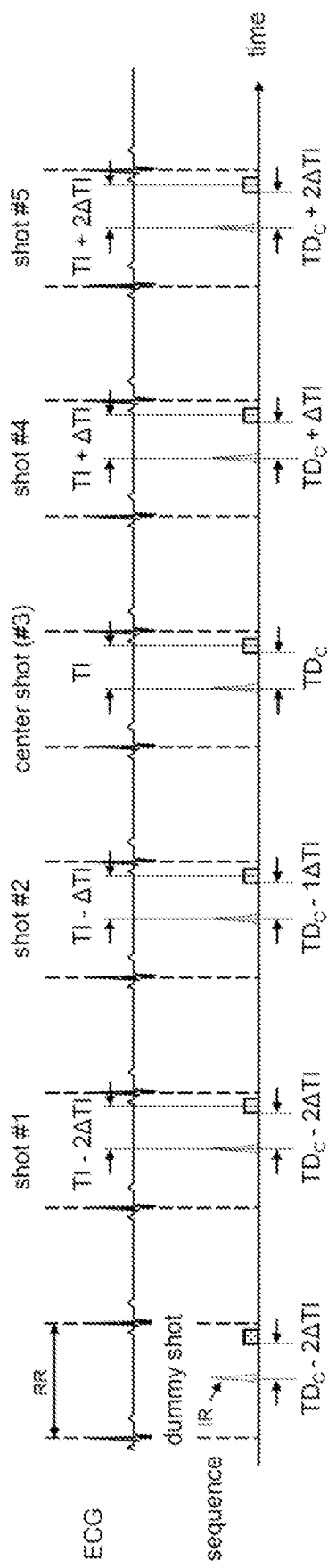
FIG. 6 illustrates an IR-prepared segmented pulse sequence including shot-specific TI values and interleaved reordering according to some embodiments.

The concept of improving image quality using a different TI during acquisition of the DCS of each shot can also be applied to interleaved reordering. This approach may reduce or remove the above-mentioned small steps in the modulation function and thus prevent the slight ghosting which is inherent to interleaved reordering. FIG. 6 shows an IR-prepared segmented sequence with interleaved reordering, where TD is adjusted per shot and is based on a TI determined for the center line-acquiring segment.

Center shot #3 includes a delay $TD_C$ from the peak of its inversion pulse to the beginning of acquisition of its DCS. $TD_C$ is equal to a pre-selected TI minus half the number of lines acquired per shot multiplied by the echo spacing (ES). The time delay TD between the IR pulse and acquisition of the DCS of shot #2 is $TD_C-1\Delta TI$, where $\Delta TI$ is equal to ES/N, and where N is the number of shots in the sequence.

Figure 3A:
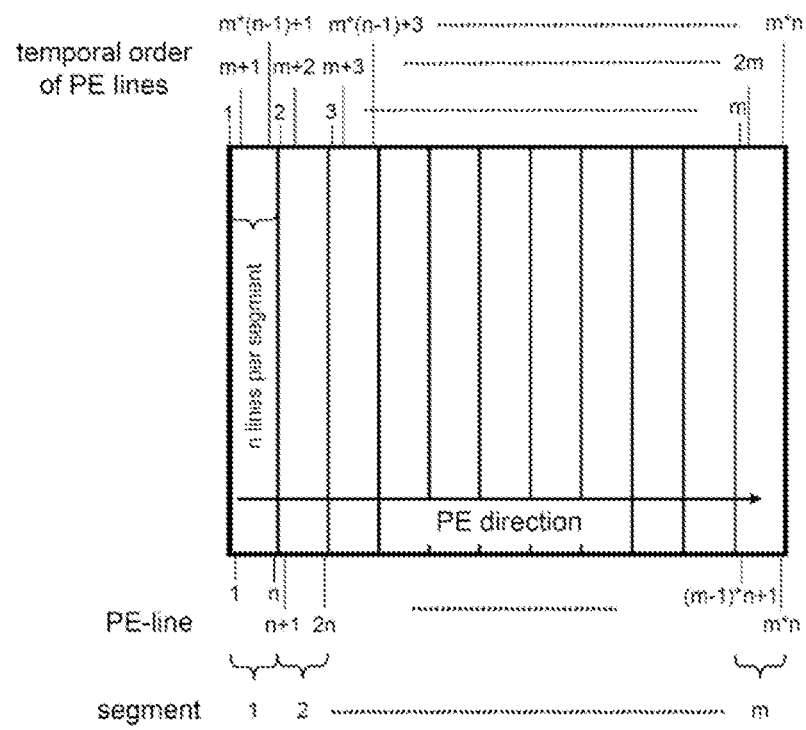
FIG. 3A illustrates interleaved reordering.
Figure 3B:
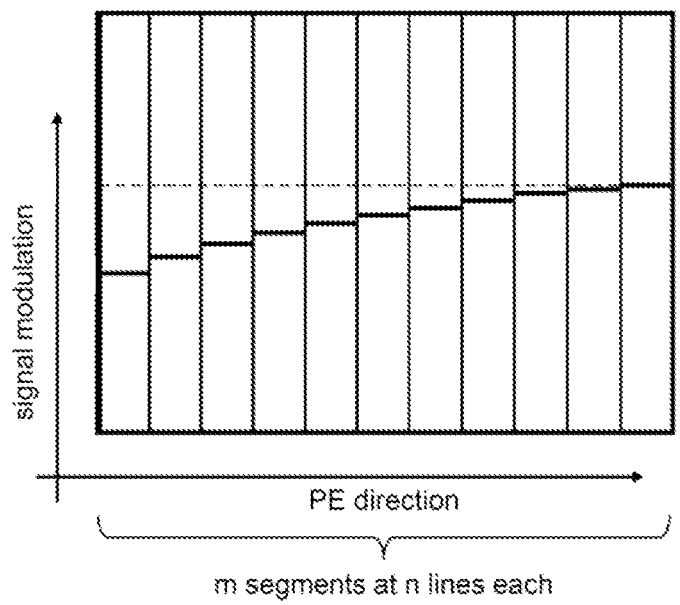
FIG. 3B illustrates modulation discontinuities within k-space due to interleaved reordering.
Figure 7:
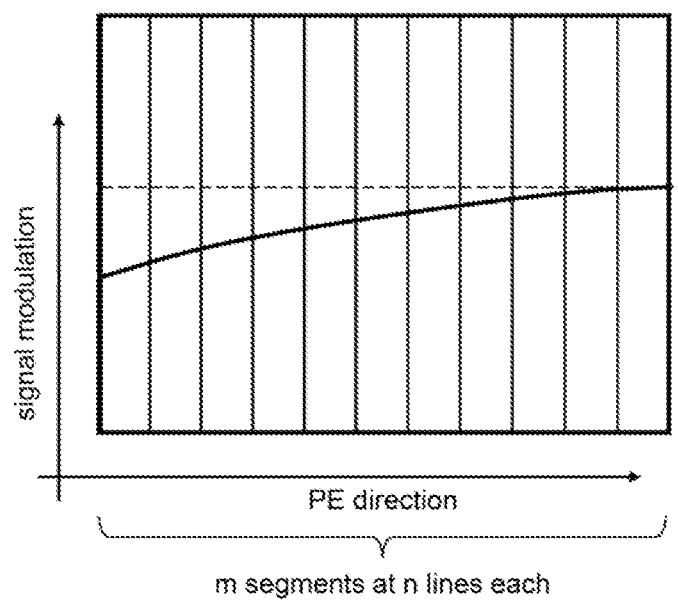
FIG. 7 illustrates signal modulation across k-space exhibited by the IR-prepared segmented pulse sequence of FIG. 6.

Continuing this logic, the time delay TD between the IR pulse and acquisition of the DCS of shot #1 is $TD_C-2\Delta TI$. Conversely, the time delay TD for shot #4 is increased by $\Delta TI$ to $TD_C+1\Delta TI$, and for shot #5 by $2\Delta TI$ to $TD_C+2\Delta TI$. The modulation function of interleaved reordering using the foregoing timings is shown in FIG. 7. The constant modulation in each segment shown in FIG. 3B is now a T1-recovery modulation that is smooth across segment borders. A modified interleaved reordering as illustrated in FIG. 6 may therefore offer improved image quality for static objects but suffers from the same motion-sensitivity as the conventional interleaved reordering described above.

Figure 8:
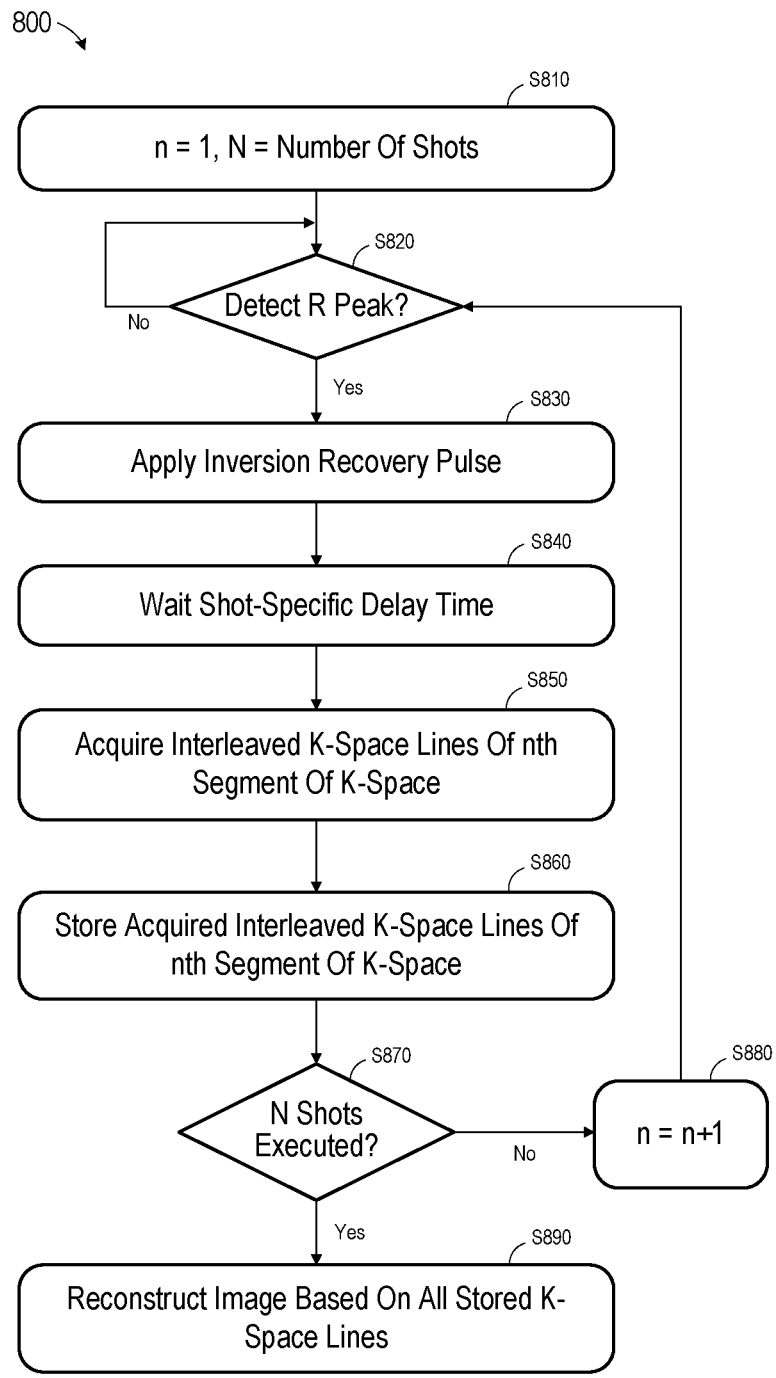
FIG. 8 is a flow diagram of a process to execute the FIG. 6 pulse sequence according to some embodiments.

Process 800 of FIG. 8 may be performed to execute the sequence of FIG. 6 in some embodiments. Again, the shot number n is initialized to 1 at S810 and N represents the number of shots to be executed. Flow pauses at S820 until an R peak (i.e., the start of a heartbeat interval) is detected. At S830, an IR pulse is applied at a timing specific to the first (n=1) shot. The timing of the IR pulse is determined based on $TD_C$ and on the temporal location of the present shot with respect to the center shot. As mentioned above, the IR pulse of shot #1 is applied such that its peak is $TD_C-2\Delta TI$ from the beginning of the acquisition of the DCS of shot #1, where $\Delta TI$ is equal to ES/N. As described with respect to FIG. 4, each IR pulse of the FIG. 6 pulse sequence is applied at a different time interval from its preceding R peak.

Process 800 waits at S840 for a shot-specific delay time before applying its DCS at S850. Accordingly, unlike the FIG. 4 sequence, the TD between the peak of the inversion pulse of each shot and the beginning of acquisition of its first (and only) segment differs for each shot of the FIG. 6 sequence. However, similarly to the FIG. 6 sequence, the TI between the inversion pulse peak of each shot and the center of its DCS acquisition differs for each shot.

Next, at S850, a segment is applied to acquire interleaved k-space lines of an nth segment of k-space as described above. The interleaved k-space lines are stored at S860, and flow continues in this manner for each successive shot until it is determined at S870 that M shots have been executed. As described above with respect to process 500, flow may pause at S820 until two R peaks are detected in order to allow a magnetization recovery heartbeat interval to elapse between consecutive shots as illustrated in FIG. 6. Once M shots have been executed, an image is reconstructed at S890 based on all the stored interleaved k-space lines as is known in the art.

Figure 9:
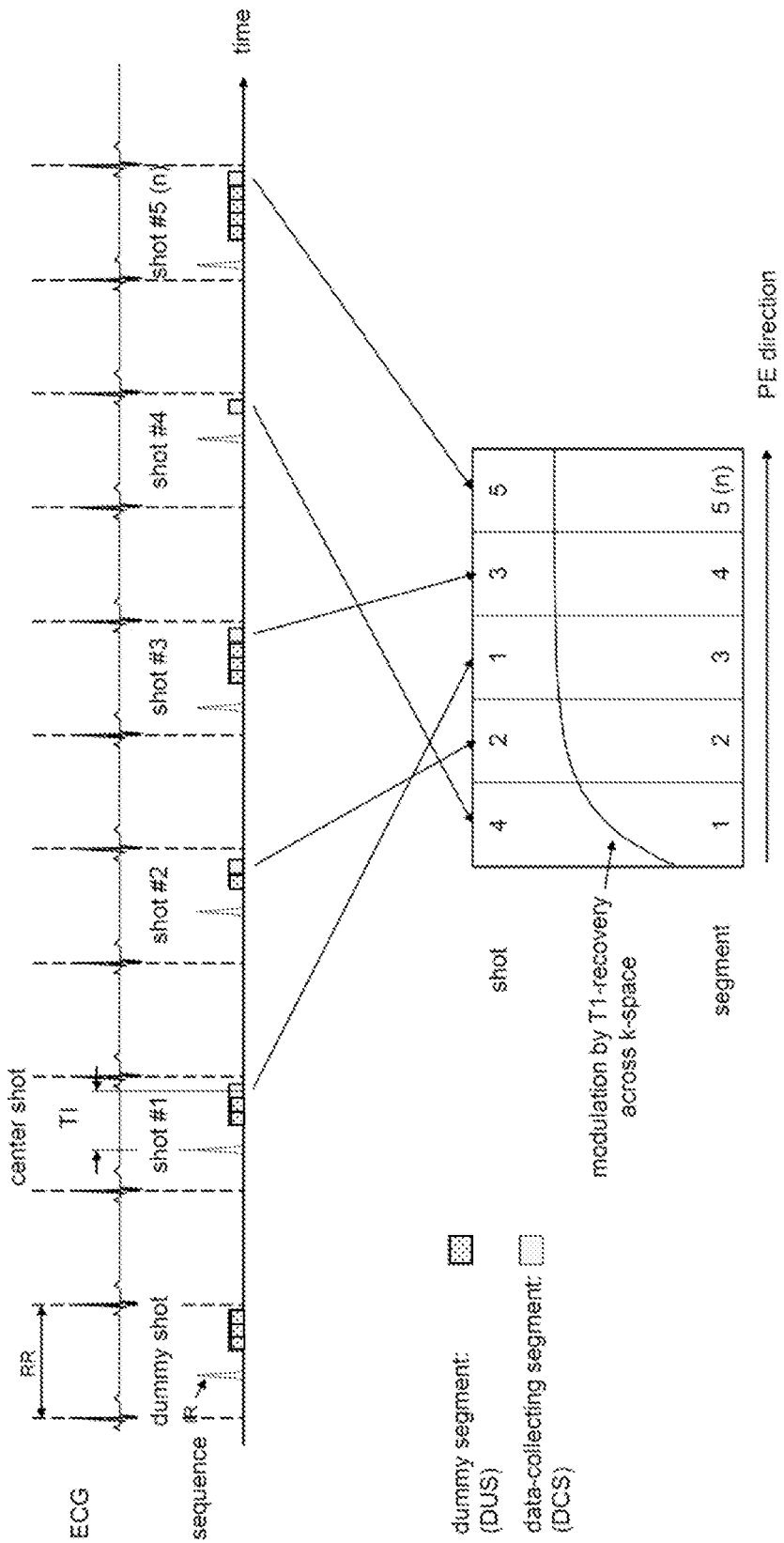
FIG. 9 illustrates an IR-prepared segmented pulse sequence including shot-specific TI values and acquisition of dummy segments according to some embodiments.

The order in which segments of k-space lines are acquired can be varied from that shown in FIG. 4. For example, it may be advantageous to acquire the center segment in shot #1, then the segments adjacent to the center segment in shots #2 and #3, and the outside segments (i.e., 1 and 5) in shots #4 and #5. FIG. 9 illustrates such a sequence according to some embodiments.

Advantageously, after the first shot, a full field of view intermediate image can be reconstructed based on the acquired center segment of k-space lines. This image is of low spatial resolution in the PE direction, but without fold-in artifacts. After acquisition of segments 2 and 4 by shots #2 and #3, segments 2, 3 and 4 may be used to reconstruct a second intermediate image with triple the PE-resolution of the first image. A full PE-resolution image can be reconstructed after executing shots #4 and #5 to acquire segments 1 and 5. The intermediate images may be displayed during acquisition in real-time as they are reconstructed.

The sequence of FIG. 9 allows for stopping the sequence once the desired spatial resolution is obtained, where the spatial resolution improves with scan time. In a variation on the FIG. 9 sequence, an intermediate image is reconstructed after acquisition of the center segment and also after acquisition of the center segment and one adjacent segment, using a partial Fourier reconstruction. For example, a second intermediate image would be reconstructed from segments 3 and 2, and a third intermediate image would be reconstructed from segments 3, 2, 4, and 1. In contrast, execution of all shots is required before any image can be reconstructed from interleaved-reordered lines.

Figure 10:
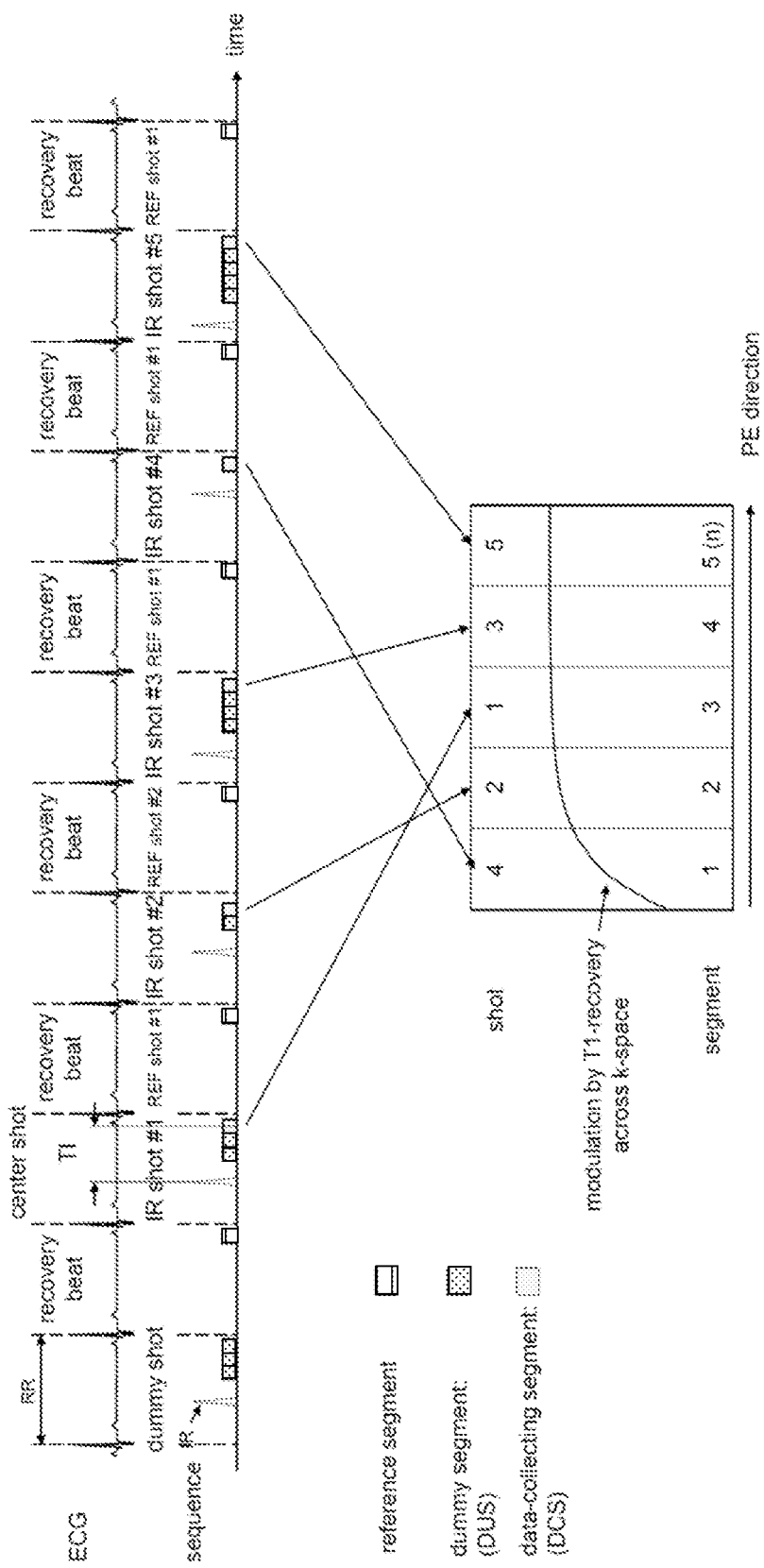
FIG. 10 illustrates an IR-prepared segmented pulse sequence including shot-specific TI values, acquisition of dummy segments and recovery beat reference segments according to some embodiments.

FIG. 10 illustrates a sequence in which the FIG. 9 sequence is used with phase-sensitive IR (PSIR) imaging. As is known in the art, a PSIR sequence reconstructs real (i.e., sign-true) images to overcome an operator's imperfect TI choice. During the sequence, a reference segment is acquired during the recovery beats. The reference segment acquires the same contiguous lines of k-space as the image data acquired by the following shot and is used to restore the true sign of the image data acquired by the following shot.

Figure 11:
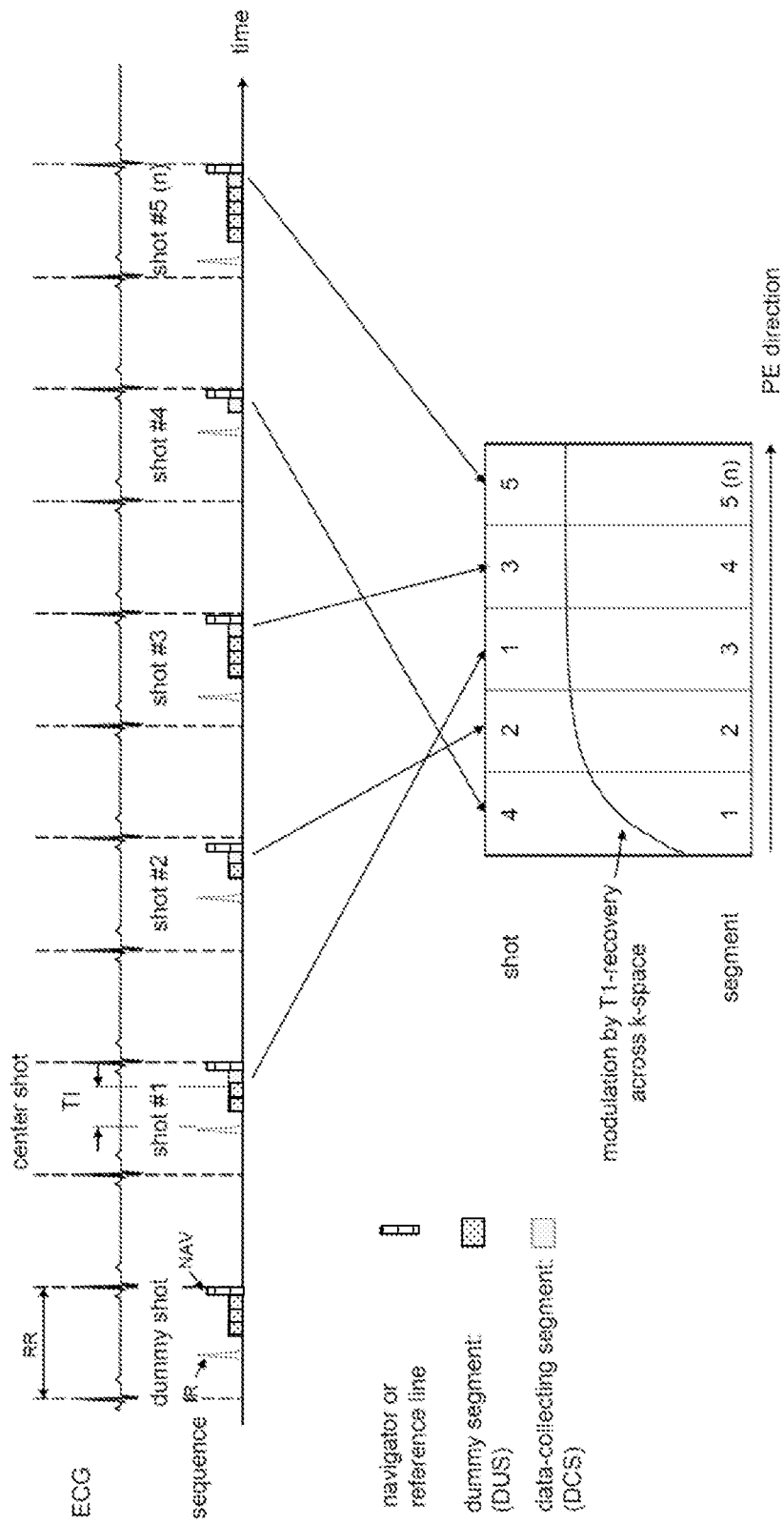
FIG. 11 illustrates an IR-prepared segmented pulse sequence including shot-specific TI values, acquisition of dummy segments and navigator pulses according to some embodiments.

The motion-robust embodiments described herein can be combined with the acquisition of a respiratory navigator, a reference line, or a low-resolution reference image. This allows free-breathing acquisitions without ghosting, which would be observed if using interleaved reordering. FIG. 11 shows the same sequence as in FIG. 9, in which each shot includes an additional acquisition of a respiratory navigator echo or reference line immediately after acquisition of a DCS. The respiratory navigator echo or reference line may include the center-k-space line and may be used to determine if the acquired DCS comes from the same respiratory phase as the DCSs of the previous shots. If so, the acquired DCS is kept, otherwise it is reacquired.

Figure 12:
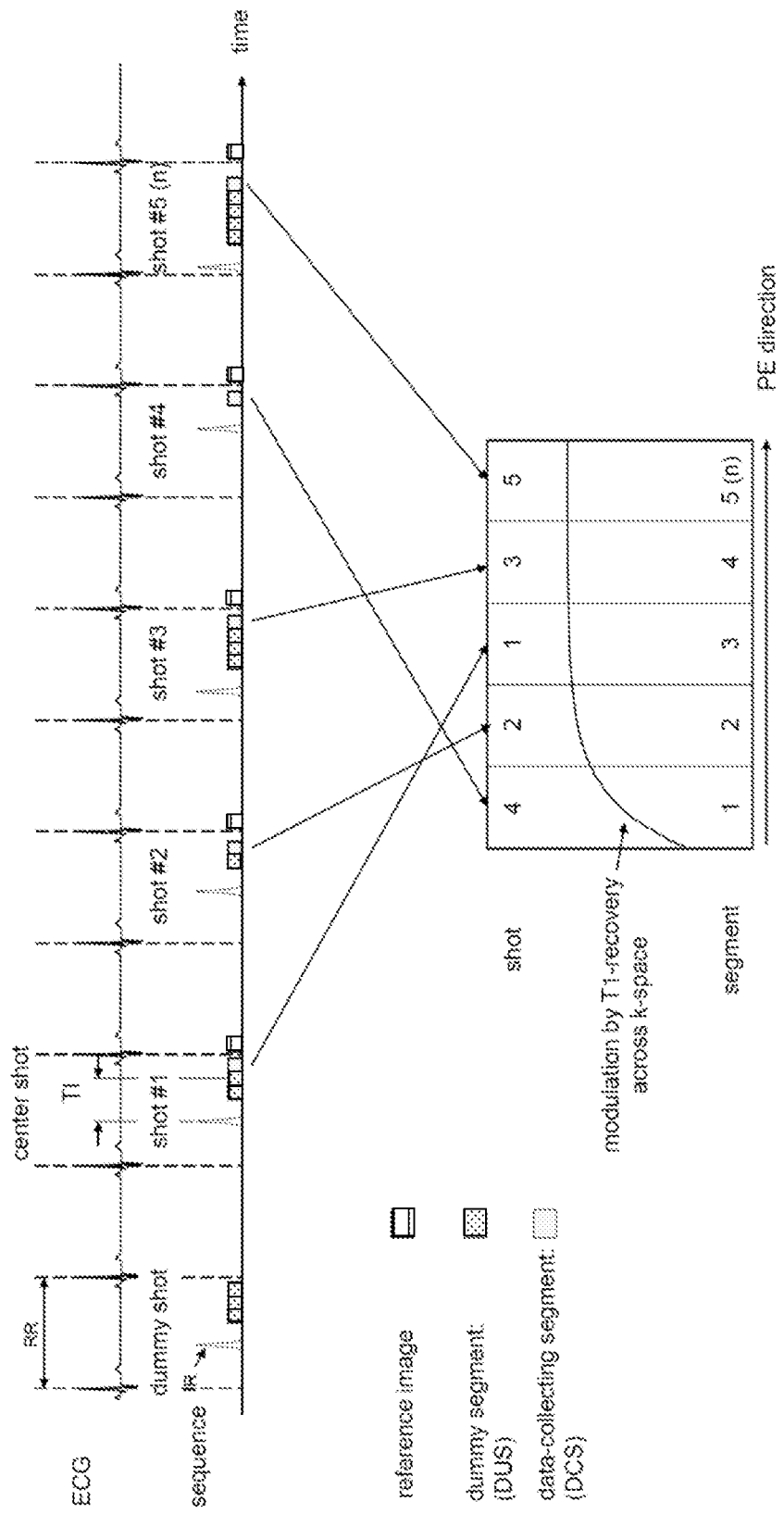
FIG. 12 illustrates an IR-prepared segmented pulse sequence including shot-specific TI values, acquisition of dummy segments and recovery beat reference segments according to some embodiments.

FIG. 12 shows a sequence similar to the sequence of FIG. 11. However, instead of acquiring a single reference line per shot, a low-PE resolution reference image is acquired at the R-wave following acquisition of a respective DCS. This reference image can be advantageously used for PSIR reconstruction. The reference image can also be used to decide if the DCS segment was acquired at the same/similar respiratory phase as all other DCSs. Moreover, the low-resolution reference image can be used to perform motion correction on the image reconstructed from the prior DCS segment. This is not possible with interleaved reordering since each shot of interleaved reordering acquires data that, by itself, can only be reconstructed into an aliased image, which by definition cannot be suitably processed by a non-rigid motion correction algorithm.

Although the sequences described herein use an ECG signal as a triggering source, embodiments are compatible with any other means of triggering, such as pulse oximetry, a respiratory belt, an inductively coupled device, or a Pilot Tone device. Embodiments may be implemented without triggering by using a constant effective time-to-repeat (effective TR) in place of the above-described R-R interval.

Figure 13:
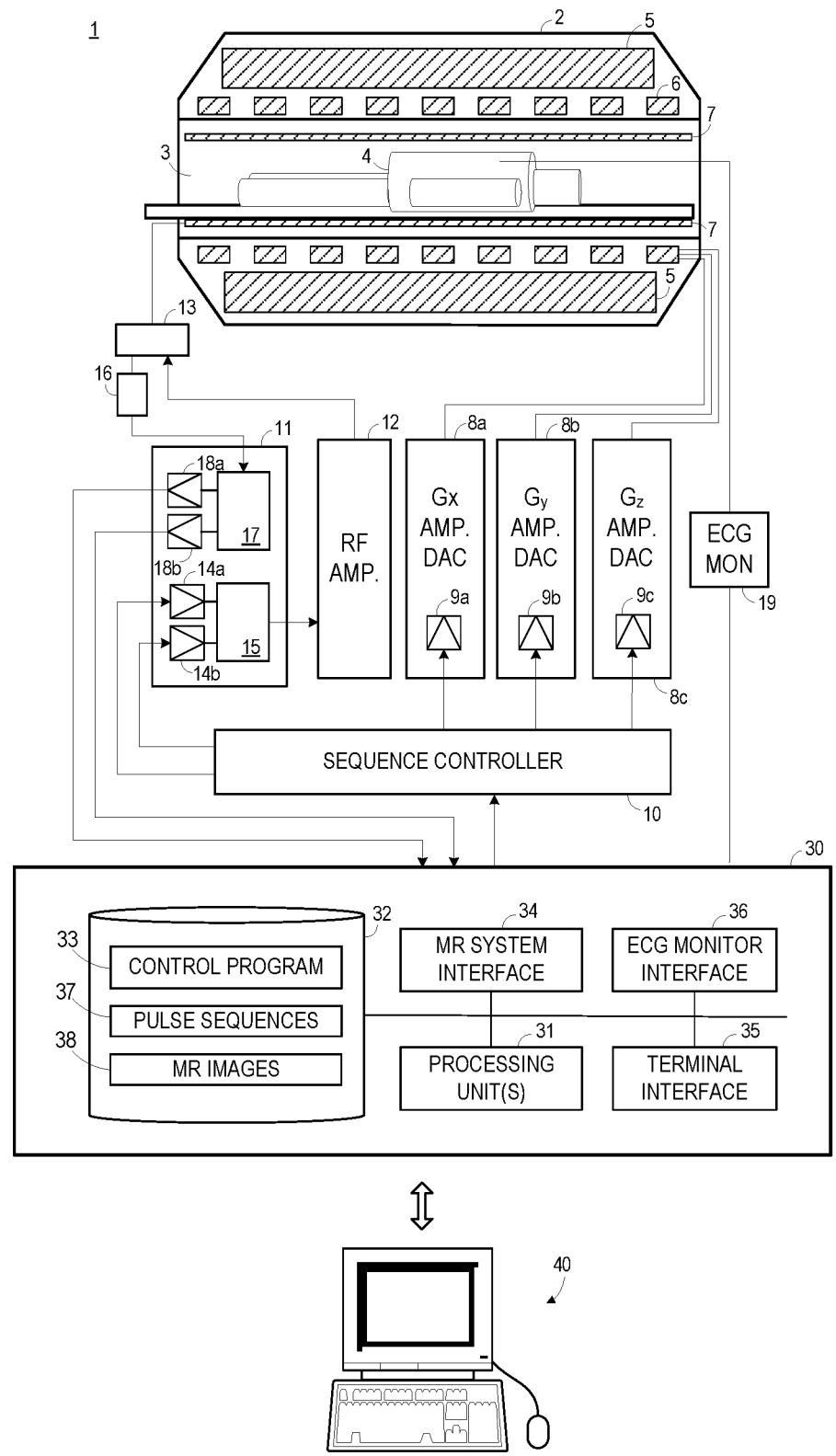
FIG. 13 is a block diagram of an example MRI system for use in some embodiments.

FIG. 13 illustrates MR system 1 according to some embodiments. MR system 1 includes MR chassis 2, which defines bore 3 in which patient 4 is disposed. MR chassis 2 includes polarizing main magnet 5, gradient coils 6 and RF coil 7 arranged about bore 3. According to some embodiments, polarizing main magnet 5 generates a uniform main magnetic field ($B_0$) and RF coil 7 emits an excitation field ($B_1$).

According to MR techniques, a substance (e.g., human tissue) is subjected to a main polarizing magnetic field (i.e., $B_0$), causing the individual magnetic moments of the nuclear spins in the substance to process about the polarizing field in random order at their characteristic Larmor frequency, in an attempt to align with the field. A net magnetic moment $M_z$ is produced in the direction of the polarizing field, and the randomly-oriented magnetic components in the perpendicular plane (the x-y plane) cancel out one another.

The substance is then subjected to an excitation field (i.e., $B_1$) created by emission of a radiofrequency (RF) pulse, which is in the x-y plane and near the Larmor frequency, causing the net aligned magnetic moment $M_z$ to rotate into the x-y plane so as to produce a net transverse magnetic moment $M_t$, which is rotating, or spinning, in the x-y plane at the Larmor frequency. The excitation field is terminated, and signals are emitted by the excited spins as they return to their pre-excitation field state. The emitted signals are detected, digitized and processed to reconstruct an image or a spectrum using one of many well-known MR techniques.

Gradient coils 6 produce magnetic field gradients $G_x$, $G_y$, and $G_z$ which are used for position-encoding NMR signals. The magnetic field gradients $G_x$, $G_y$, and $G_z$ distort the main magnetic field in a predictable way so that the Larmor frequency of nuclei within the main magnetic field varies as a function of position. Accordingly, an excitation field $B_1$ which is near a particular Larmor frequency will tip the net aligned moment $M_z$ of those nuclei located at field positions which correspond to the particular Larmor frequency, and signals will be emitted only by those nuclei after the excitation field $B_1$ is terminated.

Gradient coils 6 may consist of three windings, for example, each of which is supplied with current by an amplifier 8a-8c in order to generate a linear gradient field in its respective Cartesian direction (i.e., x, y, or z). Each amplifier 8a-8c includes a digital-analog converter 9a-9c which is controlled by a sequence controller 10 to generate desired gradient pulses at prescribed times.

Sequence controller 10 also controls the generation of RF pulses by RF system 11 and RF power amplifier 12. RF system 11 and RF power amplifier 12 are responsive to a scan prescription and direction from sequence controller 10 to produce RF pulses of the desired frequency, phase, and pulse amplitude waveform. The generated RF pulses may be applied to the whole of RF coil 7 or to one or more local coils or coil arrays. RF coil 7 converts the RF pulses emitted by RF power amplifier 12, via multiplexer 13, into a magnetic alternating field in order to excite the nuclei and align the nuclear spins of the object to be examined or the region of the object to be examined. As mentioned above, RF pulses may be emitted in a magnetization preparation step in order to enhance or suppress certain signals.

The RF pulses are represented digitally as complex numbers. Sequence controller 10 supplies these numbers in real and imaginary parts to digital-analog converters 14a-14b in RF system 11 to create corresponding analog pulse sequences. Transmission channel 15 modulates the pulse sequences with a radio-frequency carrier signal having a base frequency corresponding to the resonance frequency of the nuclear spins in the volume to be imaged.

RF coil 7 both emits radio-frequency pulses as described above and scans the alternating field which is produced as a result of processing nuclear spins, i.e., the nuclear spin echo signals. The received signals are received by multiplexer 13, amplified by RF amplifier 16 and demodulated in receiving channel 17 of RF system 11 in a phase-sensitive manner. Analog-digital converters 18a and 18b convert the demodulated signals into digitized real and imaginary components.

Electrocardiograph ("ECG") monitor 19 acquires ECG signals from electrodes placed on patient 4. Such physiological signals may be used by sequence controller 10 to synchronize, or "gate", transmitted RF pulses of a spectroscopy pulse sequence based on the heartbeat of patient 4 as described herein.

Computing system 30 receives the digitized real and imaginary components from analog-digital converters 18a and 18b and may process the components according to known techniques. Such processing may, for example, include reconstructing two-dimensional or three-dimensional images by performing a Fourier transformation of raw k-space data, performing other image reconstruction techniques such as iterative or back-projection reconstruction techniques, applying filters to raw k-space data or to reconstructed images, generating functional magnetic resonance images, calculating motion or flow images, and generating a chemical shift vs. magnitude spectrum.

System 30 may comprise any general-purpose or dedicated computing system. Accordingly, system 30 includes one or more processing units 31 (e.g., processors, processor cores, execution threads, etc.) configured to execute processor-executable program code to cause system 30 to operate as described herein, and storage device 32 for storing the program code. Storage device 32 may comprise one or more fixed disks, solid-state random access memory, and/or removable media (e.g., a thumb drive) mounted in a corresponding interface (e.g., a USB port).

One or more processing units 31 may execute program code of control program 33 to provide instructions to sequence controller 10 via MR system interface 34. For example, sequence controller 10 may be instructed to initiate a desired pulse sequence of pulse sequences 37. In particular, sequence controller 10 may be instructed to control the switching of magnetic field gradients via amplifiers 8a-8c at appropriate times, the transmission of radio-frequency pulses having a specified phase and amplitude at specified times via RF system 11 and RF amplifier 12, and the readout of the resulting MR signals. The timing of the various pulses of a pulse sequence may be based on physiological data received by ECG monitor interface 36.

Storage device 32 stores MR images 38 generated as described herein. Such images may be provided to terminal 40 via terminal interface 35 of system 30. Terminal interface 35 may also receive input from terminal 40, which may be used to provide commands to control program 33 in order to initiate single-voxel spectroscopy as described herein. Terminal 40 may comprise a display device and an input device coupled to system 30. In some embodiments, terminal 40 is a separate computing device such as, but not limited to, a desktop computer, a laptop computer, a tablet computer, and a smartphone.

Each element of system 1 may include other elements which are necessary for the operation thereof, as well as additional elements for providing functions other than those described herein. Storage device 32 may also store data and other program code for providing additional functionality and/or which are necessary for operation of system 30, such as device drivers, operating system files, etc.

Executable program code according to the above description may be stored on a form of non-transitory computer-readable media. Computer-readable media includes volatile and nonvolatile, removable, and non-removable media implemented in any method or technology for storage of information such as program code, data structures, program modules or other data. Computer-readable media includes, but is not limited to, random access memory (RAM), read-only memory (ROM), electrically erasable programmable ROM (EEPROM), flash memory or other memory technology, compact disk ROM (CD-ROM), digital volatile disks (DVD) or other optical storage, magnetic cassettes, magnetic tape, magnetic disk storage or other magnetic storage devices, or any other medium which can be used to store the desired instructions and which may be accessed by a system (e.g., a computer), including by internet or other computer network form of access.

The foregoing diagrams represent logical architectures for describing processes according to some embodiments, and actual implementations may include more or different components arranged in other manners. Other topologies may be used in conjunction with other embodiments. Moreover, each component or device described herein may be implemented by any number of devices in communication via any number of other public and/or private networks. Two or more of such computing devices may be located remote from one another and may communicate with one another via any known manner of network(s) and/or a dedicated connection. Each component or device may comprise any number of hardware and/or software elements suitable to provide the functions described herein as well as any other functions. For example, any computing device used in an implementation of a system according to some embodiments may include a processor to execute program code such that the computing device operates as described herein.

Embodiments described herein are solely for the purpose of illustration. Those in the art will recognize other embodiments may be practiced with modifications and alterations to that described above.

What is claimed is:

1. A magnetic resonance imaging system comprising:
a magnet system configured to generate a polarizing magnetic field about at least a portion of a subject;
a plurality of gradient coils configured to apply at least one gradient field to the polarizing magnetic field;
a radio frequency (RF) system configured to apply an excitation field to the subject and to acquire magnetic resonance (MR) data from the subject; and
a processing unit to execute program code to cause the system to:
execute a segmented magnetic resonance imaging pulse sequence, the pulse sequence including a plurality of shots, each of the plurality of shots including an inversion recovery preparation pulse and readout pulses to acquire a respective segment of k-space lines, wherein a time between a peak of the inversion recovery pulse and a midpoint of the readout pulses to acquire the respective segment of k-space lines is different for each of the plurality of shots;
combine the acquired respective segments of k-space lines into one k-space;
reconstruct an image from the one k-space; and
present the image on a display.

2. A method comprising:
executing a segmented magnetic resonance imaging pulse sequence, the pulse sequence including a plurality of shots, each of the plurality of shots including an inversion recovery preparation pulse and readout pulses to acquire a respective segment of k-space lines, wherein a time between a peak of the inversion recovery pulse and a midpoint of the readout pulses to acquire the respective segment of k-space lines is different for each of the plurality of shots;
combining the acquired respective segments of k-space lines into one k-space;
reconstructing an image based on a combination of the acquired respective segments of k-space lines into one k-space; and
presenting the image.

3. A non-transitory computer-readable medium storing program code executable by one or more processing units to cause a computing system to:
execute a segmented magnetic resonance imaging pulse sequence, the pulse sequence including a plurality of shots, each of the plurality of shots including an inversion recovery preparation pulse and readout pulses to acquire a respective segment of k-space lines, wherein a time between a peak of the inversion recovery pulse and a midpoint of the readout pulses to acquire the respective segment of k-space lines is different for each of the plurality of shots;
combine the acquired respective segments of k-space lines into one k-space;
reconstruct an image from the one k-space; and
present the image on a display.

4. A system according to claim 1, wherein the k-space lines acquired by the readout pulses of each shot are consecutive in a phase encoding direction of k-space,
wherein the readout pulses of each shot acquire the segments of k-space lines acquired by the readout pulses of prior shots in the sequence, and
wherein the acquired segments of k-space lines acquired by the readout pulses of prior shots are not used to reconstruct the image.

5. A system according to claim 1, wherein the readout pulses of each shot acquire their respective segment using interleaved reordering.

6. A method according to claim 2, wherein the k-space lines acquired by the readout pulses of each shot are consecutive in a phase encoding direction of k-space,
wherein the readout pulses of each shot acquire the segments of k-space lines acquired by prior shots in the sequence, and
wherein the acquired segments of k-space lines acquired by the readout pulses of prior shots are not used to reconstruct the image.

7. A method according to claim 2, wherein the readout pulses of each shot acquire their respective segment using interleaved reordering.

8. A medium according to claim 3, wherein the k-space lines acquired by the readout pulses of each shot are consecutive in a phase encoding direction of k-space,
wherein the readout pulses of each shot acquire the segments of k-space lines acquired by the readout pulses of prior shots, and
wherein the acquired segments of k-space lines acquired by the readout pulses of prior shots are not used to reconstruct the image.

9. A medium according to claim 3, wherein the readout pulses of each shot acquire their respective segment using interleaved reordering.

10. A system according to claim 4, wherein a time delay between the inversion recovery preparation pulse and acquisition of a first segment for each shot is equal.

11. A system according to claim 5, wherein a time delay between the inversion recovery preparation pulse and acquisition of the respective segment is different for each shot.

12. A method according to claim 6, wherein a time delay between the inversion recovery preparation pulse and acquisition of a first segment for each shot is equal.

13. A method according to claim 7, wherein a time delay between the inversion recovery preparation pulse and acquisition of the respective segment is different for each shot.

14. A medium according to claim 8, wherein a time delay between the inversion recovery preparation pulse and acquisition of a first segment for each shot is equal.

15. A medium according to claim 9, wherein a difference in the time delay between the inversion recovery preparation pulse and acquisition of the respective segment for consecutive shots is equal to ES/N, where ES is the echo spacing of the acquisition and N is the total number of shots in the sequence.

16. A system according to claim 10, wherein the readout pulses of a first-in-time shot of the sequence acquire a first segment including a center line of k-space, wherein the readout pulses of a second-in-time shot of the sequence acquire a second segment sharing a first border with the first segment, and the readout pulses of a third-in-time shot of the sequence acquire a third segment sharing a second border with the first segment, the processing unit to execute program code to cause the system to:
  reconstruct a first intermediate image from the first segment and no other segments; and
  reconstruct a second intermediate image from the first segment, the second segment, the third segment and no other segments.

17. A system according to claim 11, wherein a difference in the time delay between the inversion recovery preparation pulse and acquisition of the respective segment for consecutive shots is equal to ES/N, where ES is the echo spacing of the acquisition and N is the total number of shots in the sequence.

18. A method according to claim 12, wherein the readout pulses of a first-in-time shot of the sequence acquire a first segment including a center line of k-space, wherein the readout pulses of a second-in-time shot of the sequence acquire a second segment sharing a first border with the first segment, and the readout pulses of a third-in-time shot of the sequence acquire requires a third segment sharing a second border with the first segment, the method further comprising:
  reconstructing a first intermediate image from the first segment and no other segments; and
  reconstructing a second intermediate image from the first segment, the second segment, the third segment and no other segments.

19. A method according to claim 13, wherein a difference in the time delay between the inversion recovery preparation pulse and acquisition of the respective segment for consecutive shots is equal to ES/N, where ES is the echo spacing of the acquisition and N is the total number of shots in the sequence.

20. A medium according to claim 14, wherein the readout pulses of a first-in-time shot of the sequence acquire a first segment including a center line of k-space, wherein the readout pulses of a second-in-time shot of the sequence acquire a second segment sharing a first border with the first segment, and the readout pulses of a third-in-time shot of the sequence acquires a third segment sharing a second border with the first segment, the program code executable by one or more processing units to cause a computing system to:
  reconstruct a first intermediate image from the first segment and no other segments; and
  reconstruct a second intermediate image from the first segment, the second segment, the third segment and no other segments.

* * * * *